Dec. 19, 1972 N. J. FRIESEN Plant Pat. 3,273
PEACH TREE
Filed April 15, 1971
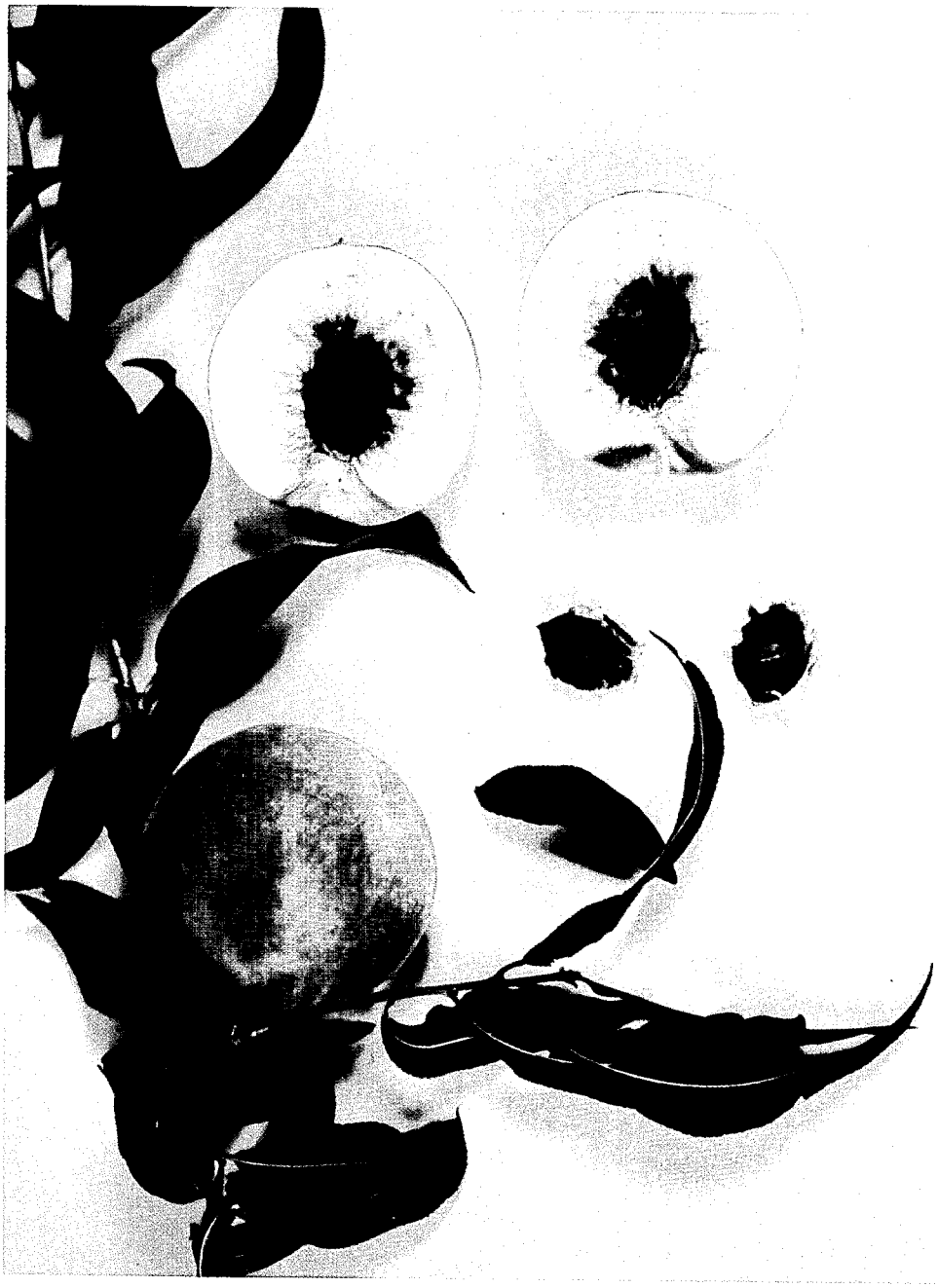
NIKOLAI J. FRIESEN
INVENTOR
Huebner & Worrel
ATTORNEYS

United States Patent Office

Plant Pat. 3,273
Patented Dec. 19, 1972

3,273

PEACH TREE

Nikolai J. Friesen, 41857 Road 42,
Reedley, Calif. 93654

Filed Apr. 15, 1971, Ser. No. 134,516
Int. Cl. A01h *5/03*
U.S. Cl. Plt.—43 1 Claim

ABSTRACT OF THE DISCLOSURE

A new and distinct variety of peach tree broadly characterized by its regular bearing of highly colored, firmly textured, early and uniformly ripening, excellently setting fruit having a minimum of fuzz.

SUMMARY OF SIGNIFICANT FEATURES OF THE NEW VARIETY

The instant variety blooms at a time which is generally regarded as early, being about the same time as the Merrill 49er peach tree (unpatented) which it most nearly resembles except that its blossoms are a somewhat brighter pink color than the redder blossoms of the 49er peach tree. Its fruit also distinguishes from the fruit of the 49er peach tree by ripening about seven to ten days earlier at about the same time as the fruit of the Sun Crest (unpatented) peach tree. The fruit of the instant variety is capable of hanging on the tree after coloring for a week to ten days before picking with the flesh thereof still being sufficiently firm to be employed for refrigerated shipping to distant markets. This also permits the fruit to be completely harvested, usually in just two pickings, as compared to the three or four pickings required by the 49er peach tree and other varieties. Furthermore, the fruit of the instant variety has a more uniformly spherical shape than the 49er with very little tip and has a sweeter flavor and less fuzz than the fruit of the 49er peach tree.

ORIGIN AND ASEXUAL REPRODUCTION OF THE NEW VARIETY

I discovered the instant variety as a sport growing on a Merrill 49er peach tree in July 1961, in my orchard on Avenue 416 between Road 40 and Road 44, Reedley, Tulare County, Calif. Scions from the new variety were limb budded and others were grafted onto a number of unidentified peach trees in an orchard consisting primarily of Red Haven (unpatented) peach trees at 41857 Road 42, Reedley, Calif. in 1962. The new variety fruited in 1964 and the fruit and tree characteristics resulting from such budding and grafting proved identical to those of the original sport.

BRIEF DESCRIPTION OF THE DRAWING

The accompanying drawing is a dye transfer color print of a photograph showing a representative branch with leaves from the subject variety and two mature fruit therefrom with one divided on its suture plane to reveal flesh coloration and pit characteristics.

DESCRIPTION OF THE NEW VARIETY

Referring more specifically to the pomological details of this new and distinct variety of peach tree, the following has been observed under the ecological conditions prevailing at my above designated orchard in Reedley, Tulare County, Calif. and is an outlined description thereof. All major color plate identifications are by reference to the Nickerson Color Fan of the American Horticultural Council.

*Tree*

Size: Medium, some spreading with shape and density determined by pruning methods.
Trunk: Medium stocky, medium rough.
Branches: Lenticels—numerous, medium sized.
Leaves: (Selected from midportion of vigorous unbranched terminal shoot—18" to 24" long).
- *Size.*—Medium.
- *Length.*—5¼" to 5¾", average 5½".
- *Width.*—1¼" to 1½", average 1⅜".
- *Form.*—Lanceolate, tip acuminate.
- *Color.*—Upper surface, dark yellowish green (10 GY 4/5). Lower surface, strong yellow green (5 GY 6/8). Midrib on underside, brilliant greenish yellow (7.5 Y 9/8).
- *Margin.*—Crenate.
- *Petiole.*—Medium length, medium slender.

Flower buds: Medium size, plump, free, pubescent.
Flowers: Generally early, February 25 to March 3, medium size.
- *Petals.*—Approximately five to each blossom.
- *Color.*—Deep purplish pink (5 RP 6/10).
- *Stamens.*—Approximately sixty to each blossom.

*Fruit*

Maturity when described, firm ripe.

Size: Medium.
- *Axial diameter.*—2½" to 2⅝", average 2 9/16" under normal environmental and horticultural conditions with usual thinning to space fruit 6" to 8" on fruit bearing branches.
- *Transverse in suture plane.*—2⅝" to 2¾", average 2 11/16".
- *At right angle to suture plane.*—2⅞" to 3", average 2 15/16".

Form: Usually uniformly symmetrical, generally globose.
- *Suture.*—Faint, inconspicuous line on one side with only slight depression.
- *Ventral surface.*—Generally rounded, slight depression at suture.
- *Cavity.*—Rounded to oblong, width ¾" to 1", depth ½" to ¾".
- *Base.*—Truncate.
- *Apex.*—Rounded.
- *Pistil point.*—Generally indistinguishable, when present, apical.

Stem:
- *Length.*—⅛" to ¼".
- *Diameter.*—⅛" to 3/16".

Skin: Medium thick.
- *Under color.*—Yellow (2.5 Y 9/9), spotted and striped with strong red (5 R 4/12) to dark red (5 R 3/7).

Flesh:
- *Color.*—From brilliant yellow (5 Y 9/9) to vivid yellow (5 Y 8/12).
- *Amygdalin.*—Moderate.
- *Juice.*—Moderate.
- *Texture.*—Generally firm.
- *Fibers.*—Few, fine and tender.
- *Ripens.*—Evenly.
- *Flavor.*—Sweet.
- *Aroma.*—Distinct.
- *Eating quality.*—Excellent.

Stone: Generally free from the flesh, with some adherence along the ventral and dorsal edges.
- *Fibers.*—Short.
- *Size.*—Length, 1⅜" to 1½", average 1 7/16"; breadth—⅞" to 1", average 15/16"; thickness—¾" to ⅞", average 13/16".

*Form.*—Generally obovate, tip acuminate.
*Base.*—Straight to slightly oblique.
*Hilum.*—Oval.
*Tip.*—Acuminate.
*Sides.*—Usually equal.
*Surface.*—Irregularly furrowed particularly near apex.
*Ridges.*—Jagged.
*Pits.*—Generally oval.
*Ventral edge.*—Thick, with some ridges.
*Dorsal edge.*—Narrow, with small ridges.
*Color.*—Moderate yellowish brown (10 YR 4/4) with furrows at apex moderate red (2.5 R 4/10).

Use: Fresh market, local and distant, culinary.
*Keeping quality.*—Excellent.
*Shipping quality.*—Excellent.

Although the new variety of peach tree possesses the described characteristics under the growing conditions prevailing in Tulare County, Calif., in the central portion of the San Joaquin Valley, it is to be understood that variations of the usual magnitude in characteristics incident to changes in growing conditions, fertilization, pruning and pest control are to be expected.

Having thus described and illustrated my new variety of peach tree, what is claimed as new and desired to be secured by Letters Patent is:

1. A new and distinct variety of peach tree substantially as illustrated and described and which is characterized by its regular and heavy bearing of highly colored, firmly textured fruit which uniformly ripens about from seven to ten days earlier than the fruit of the Merrill 49er peach tree (unpatented), which it most nearly resembles, but from which fruit it also distinguishes in its somewhat smaller but more uniform size that retains its firmness for a longer period on the tree so that the fruit can be harvested in a minimum of pickings while retaining its shipping quality.

No references cited.

ROBERT E. BAGWILL, Primary Examiner